(12) United States Patent
Mulholland et al.

(10) Patent No.: US 6,561,008 B1
(45) Date of Patent: May 13, 2003

(54) DETERMINATION OF OXYGEN PERMEATION INTO CONTAINERS

(75) Inventors: Lindsay Mulholland, Cambridge (CA); Shawn Campbell, Guelph (CA); Paul Sedlak, Guelph (CA); E. Donald Murray, Eden Mills (CA)

(73) Assignee: Guelph Food Technology Centre, Guelph (CA)

( * ) Notice: Subject to any disclaimer, the term of this patent is extended or adjusted under 35 U.S.C. 154(b) by 0 days.

(21) Appl. No.: 09/697,126

(22) Filed: Oct. 27, 2000

Related U.S. Application Data

(60) Provisional application No. 60/161,911, filed on Oct. 28, 1999, and provisional application No. 60/163,776, filed on Nov. 5, 1999.

(51) Int. Cl.$^7$ ............................................... G01N 15/08
(52) U.S. Cl. ............................................. 73/38; 73/40.7
(58) Field of Search .................................... 73/38, 40.7

(56) References Cited

U.S. PATENT DOCUMENTS

| | | | | |
|---|---|---|---|---|
| 3,480,402 A | * | 11/1969 | Jackson | 422/56 |
| 3,768,976 A | * | 10/1973 | Hu et al. | 422/58 |
| 4,552,847 A | * | 11/1985 | Bauman | 73/38 |
| 4,659,674 A | * | 4/1987 | Bauman et al. | 73/38 |
| 5,316,949 A | * | 5/1994 | Bull et al. | 436/5 |
| 5,583,047 A | * | 12/1996 | Blinka et al. | 436/5 |
| 5,663,489 A | * | 9/1997 | Thungstrom et al. | 73/40.7 |

FOREIGN PATENT DOCUMENTS

| | | | | |
|---|---|---|---|---|
| GB | 2085582 | * | 4/1982 | 73/38 |

* cited by examiner

*Primary Examiner*—Daniel S. Larkin
(74) *Attorney, Agent, or Firm*—Sim & McBurney

(57) ABSTRACT

Oxygen permeation into a sealed container is determined both quantitatively or qualitatively by determining the intensity of color development of a reduced form of indigo-carmine dye in aqueous solution in the container.

12 Claims, No Drawings

DETERMINATION OF OXYGEN PERMEATION INTO CONTAINERS

This application claims benefit of Provisional Applns. 60/161,911 filed Oct. 28, 1999 and 60/163,776 filed Nov. 5, 1999.

FIELD OF INVENTION

The present invention is concerned with the detection and determination of oxygen permeation into enclosed containers, particularly transparent containers constructed of polymeric material.

BACKGROUND TO THE INVENTION

A good barrier to oxygen is critical to ensuring retention of quality in packaged foods and beverages. The permeation of oxygen into enclosed containers, such as polyethyleneterephalate (PET) bottles, having foodstuffs therein often causes spoilage of the foodstuff. It is common practice for the food industry to test for oxygen permeation into food packages to help determine product shelf-life. One common example is transparent bottles constructed of polymeric material and containing juice drinks. While the present invention is specifically described with respect to such containers, the invention is applicable to all forms of containers which are intended to house oxygen-sensitive products.

The conventional ASTM method (S1307-90) for measuring oxygen transmission rates utilizes a gas-flush system, such as the Mocon Ox-tran system. The Mocon Ox-tran 2/60 oxygen permeability testing instrument is a gas flushing system on which empty containers are mounted on the machine and flushed with nitrogen carrier gas. The oxygen passing into the container is carried to a coulometric detector, where the oxygen is quantified in units of cc package$^{-1}$ day$^{-1}$.

SUMMARY OF INVENTION

The present invention, in one aspect, provides a novel, non-invasive, quantitative method of determining the oxygen permeance into a sealed transparent container containing an aqueous solution. The present invention makes the determination in its intended state, namely as a container for a liquid system. In accordance with one aspect of the present invention, there is provided a non-invasive quantitative method of determining the oxygen permeance into a sealed container, which comprises providing a colorless aqueous solution of a reduced form of indigo-carmine dye in the sealed container, and determining the intensity of color development of the indigo-carmine dye over time as a measure of the oxygen permeation into the sealed container.

In another aspect, the present invention provides a novel, non-invasive, qualitative method of determining the location of oxygen permeation into a sealed container. In accordance with another aspect of the present invention, there is provided a non-invasive qualitative method of determining the location of oxygen permeation into a transparent sealed container, which comprises providing an immobilized aqueous solution of a reduced form of indigo-carmine dye in the sealed container, and observing the location of color development of the sealed container as a determination of the location of oxygen permeation into the container.

The present invention is based on in-situ development of color by oxidation of the reduced form of indigo-carmine dye in aqueous solution by oxygen permeation into the transparent container. As oxygen enters the packaging system, the reduced form of the indigo-carmine dye becomes oxidized, changing from colorless to blue and deepening with intensity with increased accumulation of oxygen ingress. The overall intensity of color development within the sealed container can be measured using a spectrophotometer and the sealed container. The degree of color development is used to determine the extent of the oxygen permeation into the container over time.

The indicator system may be immobilized in a gelled form, so that the color formation is localized to the areas of the bottle where there is oxygen permeation. The latter information is useful in the design of bottles or other containers to minimize such oxygen permeation and to locate failure points of the package.

GENERAL DESCRIPTION OF INVENTION

Indigo-carmine dye is colorless in its reduced form and has a characteristic blue (indigo) color ($\lambda$max=610 nm) when oxidized. Indigo-carmine dye (Merck Index #4856) has the chemical formula:

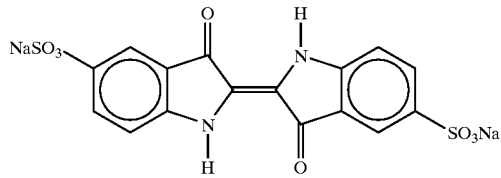

The dye is placed in aqueous solution, which first may be degassed of dissolved oxygen. The dye then is reduced using any convenient reducing agent to a colorless form. One suitable reducing agent is sodium dithionite. It is important that the reduction be effected with just sufficient reducing agent to provide the dye in a colorless form, since excessive amounts of reducing agent cause the formation of a yellow coloration with a small excess or a haziness to the solution with a larger excess. Excessive amounts of reducing agent will interfere with the spectrophotometer readings. The concentration of dye in the aqueous solution may vary widely, generally from about 0.01 to about 0.25 g/L.

The aqueous colorless dye solution is dispensed into the container to be tested, the container sealed, and color formation is monitored using a spectrophotometer. It has been found that there is a transient period during which ambient oxygen in the container is taken up by the dye solution. If a plot is made of apparent oxygen permeation over time, there is initially a steep rising slope, during the transient period, which then decreases to a flatly upwardly sloping straight line which is a true determinant of oxygen permeation. The slope of the upwardly sloping straight line is the oxygen transmission rate of the package in cc package$^{-1}$ day$^{-1}$. This transient period can be reduced by preconditioning the containers, for example, using a vitamin C solution or by filling the container with colorless dye solution and then emptying the dye solution from the container.

Precautions generally are taken to minimize the level of ambient oxygen in the containers before filling with the indicator solution at the start of the test period. This may be achieved by purging deionized water used to make up the dye solution with oxygen free gas, such as nitrogen, for example, for at least about 60 minutes. The indicator reagents, dye, and reducing agent, are sequentially mixed with the water under nitrogen and the tank containing the aqueous dye solution may be pressurized with nitrogen for delivery purposes.

Prior to filling bottles for testing, they may be purged with nitrogen, with a minimum of three volumes of nitrogen. For example, using a 500 ml container, a nitrogen flow rate of a minimum of about 500 ml/min. for approximately 3.0 min., which has the effect of removing oxygen from the container. The bottles are filled with the clear colorless dye solution under a stream of nitrogen and the headspace in the bottle purged with nitrogen prior to capping the container. Where a carbonated system is tested, the desired degree of carbonation may be achieved by purging and pressurizing the deionized water with carbon dioxide, which may be in situ produced by reacting citric acid and sodium bicarbonate, or other convenient combination of reagents, instead of using carbon dioxide as is done, for example, in standard brewing tests (American Brewing Chemists Society).

The generation of color may be determined using any convenient spectrophotometer. Once steady state oxygen transmission rates are achieved, following the transient phase mentioned above, oxygen transmission rates, reported in cc package$^{-1}$ day$^{-1}$, are calculated using linear regression analysis. The limits for acceptance of the correlation coefficient $r^2$ value is between 0.96 and 1.0.

The oxygen transmission rate is determined from the specific volume (in cc) of oxygen in a container at a specific time. The volume is determined by application of the following equations:

Beer-Lambert Law: A=bcl where:

A=absorbance
b=absorptivity (constant, in units of 100 mL/(g cm).
c=concentration (in g/100 mL).
l=path length in cm; and Ideal Gas Law: PV=nRT where:

P=pressure (atm)
V=volume (L)
n=amount of gas (mol)
T=temperature (K)
R=gas constant (0.08206 L*atm/(mol*K))

The container filled with indicator solution is placed into the spectrophotometer and measured at a specific wavelength (e.g. 650 nm), where b=149(100 ml/g.cm) which provides an absorbance (A). This absorbance translates into the concentration of dye resulted in this A value, namely:

$C_{dye}$=A/b1

Using the relationship c=n/V (usually c=mol/L, c=g/100 mL)

$$\frac{n_{(dye)}}{V_{(dye)}} = \frac{A}{bl}$$

$$n_{(dye)} = \frac{A * V_{(dye)}}{bl}$$

with units:

$$n(mols)_{(dye)} = \frac{A * V(converted\,to\,100mL\,basis)}{b(100\,mL/(g*cm))*1(cm)} * \frac{1\,mol_{(dye)}}{466.36\,g_{(dye)}}$$

$n(mols)_{(dye)} = mols_{(dye)}$

This calculation then provides the number of moles of dye producing the absorbance (A).

The stoichiometry of the color forming reaction for the indicator solution is 1 mol of $O_2$ to 2 mol of dye:

$nO_2$=mol dye * 1 mol $O_2$/2 mol dye $nO_2$=mol $O_2$ which then provides the number of moles of oxygen in the package. In order to find the volume of $O_2$ in the container, the Ideal Gas Law (relationship between pressure, volume, temperature, and amount of gas, at low pressures, see above) is used.
Therefore:

$V(O_2)=n(O_2)RT/P$

Therefore: $V(O_2) = n(O_2)RT/P$ $$= n(O_2)*0.08206\,\frac{(L*atm)}{(mol*K)}*K*\frac{1}{atm}$$

$$= L(O_2)$$

Putting these relationships together into one equation:

$$V(O_2) = \frac{A*Y(100\,mL)}{149\frac{(100\,mL)}{(g*cm)}*X(cm)} * \frac{1\,mol\,dye}{466.36\,g\,dye} *$$

$$\frac{1\,mol\,O_2}{2\,mol\,dye} * \frac{0.08206(L*atm)*Z(K)}{(mol*K)*1\,atm} * \frac{1000\,mL}{1L}$$

Variable:
X(cm)=pathlength that beam must travel through package
Y (100 mL)=volume of package
Z(K)=temperature of liquid (related to storage conditions)
A=absorbance of sealed indicator system Solving this equation then provides the volume of oxygen that has permeated the container over the experimental period. These calculations may be effected by a suitably programmed computer.

The following is an example of the variables from a typical experiment:

A=0.555 (at 650 nm, b=149)
X=6 cm
Y=475 mL (convert in terms of 100 mL=4.75 mL)
Z=298.15 K (K=273.15+° C., ∴K=25° C.+273.15)

$$V(O_2) =$$

$$\frac{0.555*4.75}{149*6}*\frac{1}{466.36}*\frac{1}{2}*\frac{0.08206}{1}*288.15*\frac{1000}{1} = 0.0773\,cc\,O_2$$

In the gelled indicator system provided herein, any convenient gel forming material may be used, such as agar gel, which is liquid at elevated temperature but takes on the form of a viscous immobile gel when cooled to ambient temperature. In preparing the bottles for testing, again precautions are taken to minimize the level of ambient oxygen in the bottle. Powdered gel material may be dispersed in freshly boiled water and dissolved. The indicator reagents then are dissolved in the resulting liquid phase of the gel matrix.

Bottles for testing are purged with nitrogen gas, such as, with a minimum of three volumes of nitrogen, which may be delivered, for example, using a 500 ml container at a flow rate of at least about 500 ml/min for approximately 3.0 min. The container is filled with warm ungelled oxygen sensitive indicator, at about 50° C. to 60° C., under a stream of nitrogen and the bottles are purged with nitrogen while being capped. The capped bottles are shaken vigorously, intermittently over a period of, say, 10 minutes, in order to disperse any developed indicator caused by oxygen that may have entered the bottle during filling. The bottles are then allowed to cool to ambient temperature and gel. A visible record, such as a digital or film photograph, may be taken to record the regions of the bottle where oxygen ingress occurs, as seen from the blue color developed at such regions.

For a carbonated system, the quantitative measurement of oxygen permeability may be combined with a determination of carbon dioxide transmission rate. In such determination, bottle weight loss is determined and, when a steady state has been reached, the determination is made and reported as grams package$^{-1}$ day$^{-1}$. The weight loss is caused by a combination of carbon dioxide loss and water loss. The carbon dioxide transmission rate is determined by the difference between the rate of total weight loss and the water vapor transmission rate, both measured at a controlled relative humidity temperature and is calculated using linear regression analysis.

The procedures provided herein have considerable advantages over prior art systems. The measurements obtained herein are obtained in a non-destructive manner and measurements are representative of the food/beverage matrix in direct contact with the package. The procedures permit testing of packages under normal or abusive storage conditions, which may simulate actual transport and/or storage conditions, such as increased temperature and relative humidity. The measurements obtained are representative of the entire packaging system, including the closures. The procedure is applicable to simulating low pH foods by adjusting the pH of the indicator solution to an appropriate value. The purging of headspace prior to capping simulates some typical filling practices.

The procedure uses an aqueous system, which is more representative of a food system. The performance of oxygen-scavenging packaging materials can be evaluated. The procedure permits a large number of samples, including rigid and flexible packages, to be rapidly tested, which is important for statistical validity. In addition, large sample sizes can be tested in a short period of time. The procedure permits modelling of carbonated beverages, such as soft drinks and beer. In the technique of the present invention, the driving force of oxygen to enter the package is more representative of a food system than the prior art.

SUMMARY OF DISCLOSURE

In summary of this disclosure, the present invention provides a non-invasive method of determining, either quantitatively or qualitatively, oxygen permeation into a variety of containers, by utilizing a change in color by indigo-carmine dye from a colorless reduced form to an oxidized colored form. Modifications are possible within the scope of the invention.

We claim:

1. A non-invasive quantitative method of determining the oxygen permeance into a sealed container, which comprises:
   providing a colorless aqueous solution of a reduced form of indigo-carmine dye in the sealed container, and
   determining the intensity of color development of the indigo-carmine dye over time as a measure of the oxygen permeation into the sealed container.

2. The method of claim 1 wherein the aqueous solution of the reduced form of indigo-carmine is first degassed to remove dissolved oxygen before the dye is placed therein.

3. The method of claim 2 wherein the indigo-carmine dye is reduced in situ in said aqueous solution using sodium dithionite.

4. The method of claim 2 wherein the indigo-carmine dye is reduced in situ with just sufficient reducing agent to provide the dye in colorless form.

5. The method of claim 1 wherein the concentration of said indigo-carmine dye is about 0.01 to about 0.25 g/L in said aqueous solution.

6. The method of claim 1 wherein the aqueous colorless dye solution is dispensed into a container to be tested and the container sealed and color development is monitored spectrophotometrically.

7. A non-invasive quantitative method of determining oxygen permeance into a sealed container, which comprises:
   dispersing a colorless aqueous solution of a reduced form of indigo-carmine dye into a container to be tested,
   sealing the container, and
   determining the intensity of color development of the indigo-carmine dye spectrophotometrically over time as a measure of oxygen permeation into the sealed container by:
     making a plot of oxygen permeation over time and making no determination of steady state oxygen permeation until an upwardly-sloping straight line plot is achieved after an initial steep rising slope, the slope of straight line plot being the oxygen transmission rate of the container.

8. A non-invasive method of determining oxygen permeance into a sealed container, which comprises:
   preconditioning the container to remove ambient oxygen,
   dispersing a colorless aqueous solution of a reduced form of indigo-carmine dye into the container to be tested,
   sealing the container, and
   determining the intensity of color development of the indigo-carmine dye spectrophotometrically over time as a measure of oxygen permeation into the sealed container by:
     making a plot of oxygen permeation over time to provide an upwardly-sloping straight line plot, the slop of which is the oxygen transmission rate of the container.

9. A non-invasive quantitative method of determining the oxygen permeance into a sealed container, which comprises:
   providing a colorless aqueous solution of a reduced form of indigo-carmine dye in the sealed container, said aqueous solution being carbonated, and
   determining the intensity of color development of the indigo-carmine dye over time as a measure of the oxygen permeation into the sealed container.

10. The method of claim 9 wherein the measurement of oxygen permeability is combined with a determination of carbon dioxide transmission rate.

11. A non-invasive qualitative method of determining the location of oxygen permeation into a transparent sealed container, which comprises:

providing an immobilized aqueous solution of a reduced form of indigo-carmine dye in the sealed container, and observing the location of color development of the sealed container as a determination of the location of oxygen permeation into the container.

12. The method of claim 11 wherein said aqueous solution of a reduced form of indigo-carmine dye is immobilized by gelling.

* * * * *